(12) United States Patent
Le-Khac et al.

(10) Patent No.: US 7,615,654 B2
(45) Date of Patent: *Nov. 10, 2009

(54) DIRECT EPOXIDATION PROCESS

(75) Inventors: Bi Le-Khac, West Chester, PA (US); Mark P. Kaminsky, Media, PA (US); Kun Qin, Chadds Ford, PA (US); Roger A. Grey, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 546 days.

This patent is subject to a terminal disclaimer.

(21) Appl. No.: 11/254,829

(22) Filed: Oct. 20, 2005

(65) Prior Publication Data

US 2007/0093668 A1   Apr. 26, 2007

(51) Int. Cl.
*C07D 301/10* (2006.01)
*C07D 303/00* (2006.01)
(52) U.S. Cl. ............... 549/513; 549/534; 549/536
(58) Field of Classification Search ........... 549/513, 549/534, 536
See application file for complete search history.

(56) References Cited

U.S. PATENT DOCUMENTS

| | | | | |
|---|---|---|---|---|
| 3,351,635 | A | 11/1967 | Kollar | 260/348.5 |
| 4,367,342 | A | 1/1983 | Wulff et al. | 549/529 |
| 4,410,501 | A | 10/1983 | Taramasso et al. | 423/326 |
| 4,833,260 | A | 5/1989 | Neri et al. | 549/531 |
| 4,994,589 | A | 2/1991 | Notermann | 549/534 |
| 5,623,090 | A | 4/1997 | Haruta et al. | 568/360 |
| 5,780,657 | A | 7/1998 | Cooker et al. | 549/534 |
| 5,824,622 | A | 10/1998 | Harmer et al. | 502/407 |
| 5,856,534 | A | 1/1999 | Cooker et al. | 549/534 |
| 6,008,388 | A | 12/1999 | Dessau et al. | 549/531 |
| 6,362,349 | B1 | 3/2002 | Kuperman et al. | 549/533 |
| 6,399,794 | B1 * | 6/2002 | Hancu | 549/533 |
| 6,498,259 | B1 | 12/2002 | Grey et al. | 549/533 |
| 6,646,142 | B1 | 11/2003 | Meima et al. | 549/536 |
| 6,958,405 | B2 | 10/2005 | Le-Khac et al. | 549/531 |
| 7,238,817 | B1 * | 7/2007 | Han | 549/538 |
| 7,432,384 | B2 * | 10/2008 | Le-Khac et al. | 549/533 |

FOREIGN PATENT DOCUMENTS

| | | |
|---|---|---|
| BE | 1001038 A7 | 6/1989 |
| EP | 0 345 856 | 12/1989 |
| JP | 4-352771 | 12/1992 |

OTHER PUBLICATIONS

R. Szostak, "Non-aluminosilicate Molecular Sieves", in *Molecular Sieves: Principles of Synthesis and Identification* (1989) pp. 205-282.
G. Vayssilov, *Catal. Rev.—Sci. Eng.* 39(3) (1997) 209.
F. Helfferich, *Ion Exchange*, Chapter 3, (1962) pp. 26-71.
A. Albright, "Basic Principles of Catalysis by Functionalized Porous Organic Polymers" in *Catalyst Supports and Supported Catalyst*, A. Stiles Ed., (1987) pp. 159-186.
Frederick J. Dechow, *Separation and Purification Techniques in Biotechnology*, Noyes Publications (1989), p. 194.

\* cited by examiner

*Primary Examiner*—Janet L. Andres
*Assistant Examiner*—Raymond Covington
(74) *Attorney, Agent, or Firm*—Yuanzhang Han

(57) ABSTRACT

A process is disclosed for the epoxidation of an olefin with hydrogen and oxygen in the presence of an oxidation catalyst comprising a transition metal zeolite, and a noble metal catalyst comprising a noble metal and an ion-exchange resin. The process is highly productive and selective in making epoxides. A noble metal catalyst comprising a cation-exchanged resin further improves the productivity and/or the selectivity of the process.

20 Claims, No Drawings

DIRECT EPOXIDATION PROCESS

FIELD OF THE INVENTION

The invention relates to a process for producing an epoxide from hydrogen, oxygen, and an olefin.

BACKGROUND OF THE INVENTION

Many different methods for the preparation of epoxides have been developed. Commercially, propylene oxide is produced by the chlorohydrin process or hydroperoxidation (see, e.g., U.S. Pat. Nos. 3,351,635 and 4,367,342; EP 0 345 856). Unfortunately, both processes have disadvantages. The chlorohydrin process suffers from the production of a dilute salt stream. The hydroperoxidation process, in which propylene is oxidized with an organic hydroperoxide such as ethylbenzene hydroperoxide or tert-butyl hydroperoxide, produces organic co-products such as t-butyl alcohol or styrene, whose value must be captured in the market place. Ethylene oxide is commercially produced by the direct oxidation of ethylene with oxygen over a silver catalyst. Unfortunately, efforts to epoxidize higher olefins (olefins containing three or more carbons) such as propylene with oxygen in the presence of a silver catalyst have failed to produce a commercial process (see, e.g., U.S. Pat. Nos. 5,856,534, 5,780,657 and 4,994,589).

Recent efforts have focused on the direct epoxidation of higher olefins with oxygen and hydrogen. For example, the reaction may be performed in the presence of a catalyst comprising gold and a titanium-containing support (see, e.g., U.S. Pat. Nos. 5,623,090, 6,362,349, and 6,646,142), or a catalyst containing palladium and a titanium zeolite (see, e.g., JP 4-352771).

Mixed catalyst systems for olefin epoxidation with hydrogen and oxygen have also been disclosed. For example, Example 13 of JP 4-352771 describes the use of a mixture of titanosilicate and Pd-on-carbon for propylene epoxidation. U.S. Pat. No. 6,008,388 describes a catalyst comprising a noble metal and a titanium or vanadium zeolite, but additionally teaches that the Pd can be incorporated into a support before mixing with the zeolite. The catalyst supports disclosed include silica, alumina, and activated carbon. U.S. Pat. No. 6,498,259 discloses the epoxidation of an olefin with hydrogen and oxygen in a solvent containing a buffer in the presence of a catalyst mixture containing a titanium zeolite and a noble metal catalyst. It also discloses that organic polymer resins such as polystyrene, styrene-divinylbenzene copolymer, crosslinked polyethyleneimines, and polybenzimidazole may be used as supports for the noble metal catalyst.

Unfortunately, these epoxidation processes typically produce unwanted by-products. For example, olefin epoxidation in the presence of oxygen and hydrogen often results in hydrogenation of the olefin, such as the formation of propane from propylene. In another undesirable reaction, oxygen and hydrogen react to make water. Such a reaction consumes hydrogen and oxygen without producing epoxides. Yet another undesirable reaction is the formation of glycols or/and glycol ethers from the reaction of the produced epoxides with solvent (e.g., water, methanol). To make the process commercially viable, further improvements in the catalyst and the process are needed.

SUMMARY OF THE INVENTION

This invention is an epoxidation process comprising reacting an olefin, hydrogen, and oxygen in the presence of an oxidation catalyst comprising a transition metal zeolite, and a noble metal catalyst comprising a noble metal and an ion-exchange resin. The process is highly productive and selective in making epoxides. A noble metal catalyst comprising a cation-exchanged resin further improves the productivity and/or the selectivity of the process.

DETAILED DESCRIPTION OF THE INVENTION

The process of the invention employs an oxidation catalyst comprising a transition metal zeolite. Zeolites generally contain one or more of Si, Ge, Al, B, P, or the like, in addition to oxygen. A transition metal zeolite is a crystalline material having a porous molecular sieve structure and containing a transition metal. A transition metal is an element in Groups 3-12 of the Periodic Table. The first row of these elements includes elements from Sc to Zn. Preferred transition metals are Ti, V, Mn, Fe, Co, Cr, Zr, Nb, Mo, and W. Particularly preferred are Ti, V, Mo, and W. Most preferred is Ti. The type of transition metal zeolite employed will depend upon a number of factors, including the size and shape of the olefin to be epoxidized. For example, it is preferred to use a relatively small pore zeolite such as a transition metal silicalite if the olefin is a lower aliphatic olefin such as ethylene, propylene, or 1-butene. Where the olefin is propylene, the use of a TS-1 (titanium silicalite-1, a titanium silicalite having an MFI topology analogous to that of the ZSM-5 aluminosilicate) is especially advantageous. For a bulky olefin such as cyclohexene, larger pore zeolites may be preferred.

Suitable titanium zeolites include titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-282). Small amounts of impurities, e.g., boron, iron, aluminum, phosphorous, copper, and the like, and mixtures thereof, may be present in the lattice. The amount of impurities is preferably less than 0.5 weight percent (wt. %), more preferably less than 0.1 wt. %. Preferred titanium silicates will generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev.-Sci. Eng.* 39(3) (1997) 209). Examples of these include TS-1, TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, and ZSM-12 are also suitable for use.

The oxidation catalyst may be used as a powder or it may be formed into particles of various shapes and sizes. Suitable oxidation catalysts have a particle size in the range of about 0.0001 to about 3 mm. The formed oxidation catalyst may be made by pelletization, spray-drying, extrudation, and the like. Additional components such as silica, alumina, titania, carbon, or other materials may be added to the oxidation catalyst (e.g., as a binder).

The noble metal catalyst comprises a noble metal. Suitable noble metals include gold, silver, platinum, palladium, iridium, ruthenium, osmium, and mixtures thereof. Preferred noble metals are Pd, Pt, Au, Re, Ag, and mixtures thereof. While any of the noble metals can be utilized, either alone or in combination, palladium and gold are particularly desirable. Typically, the amount of noble metal present in the noble metal catalyst will be in the range of from 0.01 to 20 wt. %, preferably 0.1 to 5 wt. %. The manner in which the noble metal is incorporated into the noble metal catalyst is not critical. For example, the noble metal may be supported on the ion-exchange resin by impregnation, ion exchange, adsorption, precipitation, or the like.

There are no particular restrictions regarding the choice of the noble metal compound or complex used as the source of the noble metal in the preparation of the noble metal catalyst. Suitable compounds include nitrates, sulfates, halides (e.g., chlorides, bromides), carboxylates (e.g., acetate), and amine or phosphine complexes of noble metals (e.g., palladium(ll) tetramine bromide, tetrakis(triphenylphosphine) palladium (0)).

Similarly, the oxidation state of the noble metal is not critical. Palladium, for instance, may be in an oxidation state anywhere from 0 to +4 or any combination of such oxidation states. To achieve the desired oxidation state or combination of oxidation states, the noble metal compound after being introduced into the noble metal catalyst may be fully or partially pre-reduced. Satisfactory catalytic performance can, however, be attained without any pre-reduction.

The noble metal catalyst comprises an ion-exchange resin as a support. Ion-exchange resins are synthetic organic polymers having ion-exchange properties. Examples of ion-exchange resins can be found in *Ion Exchange*, Friedrich Helfferich, McGraw-Hill Book Company, Inc. (1962), pp. 26-71. Ion-exchange resins are categorized according to functionality as either strong or weak acids or bases. Acidic resins (cationic resins) generally contain sulfonic acid or carboxylic acid groups. Basic resins (anionic resins) generally contain amine, substituted amine, ammonium, or substituted ammonium groups. Particularly preferred resins include the addition copolymers prepared from vinyl monomers. Preferably the ion-exchange resin is crosslinked.

Although gelular ion-exchange resins can be used, macroreticular ion-exchange resins are preferred. Macroreticular resins consist of agglomerates of very small gelular microspheres. They have both micropores and macropores. The average pore diameter of the resin is preferably greater than 10 angstroms (Å), more preferably greater than 20 Å. The internal surface area of the resin is typically in the range of 1-1000 square meters per gram ($m^2/g$), preferably in the range of 10-900 $m^2/g$, more preferably in the range of 30-600 $m^2/g$ (see A. L. Albright, "Basic Principles of Catalysis by Functionalized Porous Organic Polymers," in *Catalyst Supports and Supported Catalysts* (1987), A. B. Stiles, Ed., Butterworths Publishers, pp. 159-186).

Preferably, an acidic resin (cationic resin) is used. Particularly preferred resins are sulfonic acid polystyrene resins, i.e., crosslinked polystyrene containing sulfonic acid functional groups. Divinylbenzene is commonly used as the crosslinking agent. When an acidic ion-exchange resin is used, protons on the resin may be partially or completely exchanged by other cations. The extent of exchange may be anywhere in the range of 0-100 mole percent (mol. %). Preferably, at least 1 mol. % of protons are exchanged by other cations; the resulting resin is referred to as a "cation-exchanged" resin. Suitable cations include alkali metal, alkaline earth metal, lanthanide metal, zinc, cadmium, ammonium, alkylammonium, alkylphosphonium ions, and the like, and mixtures thereof. Preferred cations include alkali metal and alkaline earth metal ions, and mixtures thereof. Particularly preferred cations include sodium, potassium, calcium, and magnesium ions, and mixtures thereof.

The capacity of the ion-exchange resin is not critical. The capacity is a measure of the concentration of the functional groups (e.g., sulfonic acid or carboxylic acid, amine, ammonium, substituted ammonium) in the resin. Suitable ion-exchange resins may contain 0.01-20 equivalents per kilogram (eq/kg) of functional groups. Preferred resins contain 0.1-15 eq/kg; particularly preferred resins contain 1-10 eq/kg. For example, Amberlyst 36 (an acidic resin available from Rohm & Haas) contains 5.4 eq/kg of sulfonic acid groups. The noble metal catalyst prepared from Amberlyst 36 in Example 1 (below) contains 4.0 wt. % Na, thus about 32 mol. % of protons are exchanged by Na ions.

The noble metal catalyst may contain other support components. Suitable support components include carbon, titania, zirconia, niobia, silica, alumina, silica-alumina, titania-silica, zirconia-silica, niobia-silica, and the like, and mixtures thereof. A composite of an ion-exchange resin and any of the above components may also be used as a support for the noble metal catalyst. For instance, U.S. Pat. No. 5,824,622 discloses porous microcomposites comprising a perfluorinated ion-exchange polymer containing pendant sulfonic and/or carboxylic acid groups entrapped within and highly dispersed throughout a network of metal oxide. Similar microcomposites can be used in the present invention.

The weight ratio of oxidation catalyst:noble metal catalyst is not particularly critical. However, an oxidation catalyst: noble metal catalyst ratio of 0.01-100 (grams of oxidation catalyst per gram of noble metal catalyst) is preferred.

An olefin is required in the process. Suitable olefins include any olefin having at least one carbon-carbon double bond, and generally from 2 to 60 carbon atoms. Preferably, the olefin is an acyclic alkene of from 2 to 30 carbon atoms. The process of the invention is particularly suitable for epoxidizing $C_2$-$C_6$ olefins. More than one double bond may be present in the olefin molecule, as in a diene or triene. The olefin may be a hydrocarbon or it may contain functional groups such as halide, carboxyl, hydroxyl, ether, carbonyl, cyano, nitro groups, or the like. The process of the invention is especially useful for converting propylene to propylene oxide.

Oxygen and hydrogen are required. Although any sources of oxygen and hydrogen are suitable, molecular oxygen and molecular hydrogen are preferred. The molar ratio of hydrogen to oxygen can usually be varied in the range of $H_2$:$O_2$=1:100 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to the olefin, oxygen, and hydrogen, an inert carrier gas may be preferably used. As the carrier gas, any desired inert gas can be used. Suitable inert gases include nitrogen, helium, argon, and carbon dioxide. Saturated hydrocarbons with 1-8, especially 1-6, and preferably 1-4 carbon atoms, e.g., methane, ethane, propane, and n-butane, are also suitable. Nitrogen and saturated $C_1$-$C_4$ hydrocarbons are preferred inert carrier gases. Mixtures of the listed inert carrier gases can also be used. The molar ratio of olefin to carrier gas is usually in the range of 100:1 to 1:10 and especially 20:1 to 1:10.

The amount of oxidation catalyst used may be determined on the basis of the molar ratio of the transition metal contained in the transition metal zeolite to the olefin that is supplied per unit time. Typically, sufficient oxidation catalyst is present to provide a transition metal/olefin per hour molar feed ratio of from 0.0001 to 0.1.

The reaction mixture (excluding the oxidation catalyst and the noble metal catalyst) may be a gas, liquid, supercritical fluid, or a gas/liquid mixture under the reaction conditions. Preferably at least a portion of the reaction mixture is a liquid under the reaction conditions.

The oxidation catalyst and the noble metal catalyst are preferably in the form of a suspension or fixed-bed. The process may be performed in a continuous flow, semi-batch, or batch mode. It is advantageous to work at a pressure of 1-200 bars. Epoxidation according to the invention is carried out at a temperature effective to achieve the desired olefin epoxidation, preferably at temperatures in the range of 0-200° C., more preferably, 20-150° C.

The process preferably uses a solvent. Suitable solvents are liquid under the reaction conditions. They include, for example, oxygen-containing hydrocarbons such as alcohols, aromatic and aliphatic solvents such as toluene and hexane, chlorinated aromatic and aliphatic solvents such as chlorobenzene and methylene chloride, nitriles such as acetonitrile, carbon dioxide, and water. Suitable oxygenated solvents include alcohols, ethers, esters, ketones, carbon dioxide, water, and the like, and mixtures thereof. Preferred oxygenated solvents include water and lower aliphatic $C_1$-$C_4$ alcohols such as methanol, ethanol, isopropanol, and tert-butanol, and mixtures thereof. Fluorinated alcohols can be used.

It may be advantageous to use a buffer. The buffer is typically added to the solvent to form a buffer solution, or the solvent and buffer are added separately. The buffer solution is employed in the reaction to inhibit the formation of glycols or glycol ethers during epoxidation, and it can improve the reaction rate and selectivities. Useful buffers include any suitable salts of oxyacids, the nature and proportions of which in the mixture are such that the pH of their solutions preferably ranges from 3 to 12, more preferably from 4 to 10, and most preferably from 5 to 9. Suitable salts of oxyacids contain an anion and a cation. The anion may include phosphate, carbonate, bicarbonate, sulfate, carboxylates (e.g., acetate), borate, hydroxide, silicate, aluminosilicate, or the like. The cation may include ammonium, alkylammonium (e.g., tetraalkyl-ammoniums, pyridiniums, and the like), alkylphosphonium, alkali metal, and alkaline earth metal ions, or the like. Examples include $NH_4$, $NBu_4$, $NMe_4$, Li, Na, K, Cs, Mg, and Ca cations. The preferred buffer comprises an anion selected from the group consisting of phosphate, carbonate, bicarbonate, sulfate, hydroxide, and acetate; and a cation selected from the group consisting of ammonium, alkylammonium, alkylphosphonium, alkali metal, and alkaline earth metal ions. Buffers may preferably contain a combination of more than one suitable salt. Typically, the concentration of the buffer in the solvent is from 0.0001 M to 1 M, preferably from 0.0005 M to 0.3 M. The buffer may include ammonium hydroxide which can be formed by adding ammonia gas to the reaction system. For instance, one may use a pH=12-14 solution of ammonium hydroxide to balance the pH of the reaction system. More preferred buffers include alkali metal phosphates, ammonium phosphate, and ammonium hydroxide.

Following examples merely illustrate the invention. Those skilled in the art will recognize many variations that are within the spirit of the invention and scope of the claims.

EXAMPLE 1

Pd/Na/A36 (Catalyst A)

Amberlyst 36 resin (A36, an acidic resin obtained from Rohm & Haas) (600 mL) is washed with DIUF water (deionized and ultrafiltered, obtained from Fisher) (5×600 mL). The resin is filtered and then dried at 110° C. for 4 h, 50° C. for 3.5 h, 60° C. for 7 h, 67° C. for 8 h under vacuum, and finally at 54° C. for 64 h. The final weight of the resin is 120 g.

Into a 1-L round-bottom flask, about 500 mL of DIUF water and 0.457 g of $Pd(NH_3)_4Cl_2$ is charged. The Pd salt dissolves in the water after it is mixed for 15 min. Dry A-36 resin prepared above (33 g) is added to the $Pd(NH_3)_4Cl_2$ solution over 5 min. The slurry is placed on a rotary evaporator and mixed for 3 h under nitrogen purge while the flask is rotated at 30 rpm. The solid is filtered, then mildly rinsed with DIUF water. The filtrate contains 20 ppm Pd. The Pd/A36 resin is dried under vacuum at 60° C. for 6 h. About 31.6 g catalyst is recovered. It is placed in a calcining oven and the oven temperature is ramped at a rate of 2° C./min from 22° C. to 150° C., held at 150° C. for 8 h while the furnace is lightly purged with dry nitrogen gas containing 4 mol. % oxygen. Net weight of catalyst Pd/A36 obtained is 31.0 g.

Into a 1-L round-bottom flask, about 500 mL of DIUF water and 6.0 g of sodium dihydrogen phosphate powder is charged. The flask is swirled until the solid dissolves. The Pd/A36 made above (31.0 g) is added to the solution and the flask is placed on a rotary evaporator and rotated at 30 rpm for 3 h at 40° C. under nitrogen purge. The resin is then filtered and washed with DIUF water (4×150 mL). The filtrate contains 115 ppm Na, 0.32 wt. % P, and 0.0006 wt. % Pd. The resin is then dried in a 60° C. oven under nitrogen purge for 5.5 h. The dried resin is then placed in an oven and the oven temperature is raised from 22° C. to 110° C. at a rate of 1° C./min, then held for 2 h at 110° C. before ramping to 150° C. at a heating rate of 2° C./min, and finally held for 48 h at 150° C. The dried catalyst is then reduced in a tube reactor at 50° C. for 8 h under flow of nitrogen gas containing 5 mol. % $H_2$. The product (Catalyst A) contains 0.44 wt. % Pd, 4.0 wt. % Na, and 0.004 wt. % P.

EXAMPLE 2

Pd/$NH_4^+$/A36 (Catalyst B)

The procedure of Example 1 is repeated except that 5.58 g of ammonium dihydrogen phosphate is used instead of sodium dihydrogen phosphate with 30.3 g of Pd/A36 catalyst. The product (Catalyst B) contains 0.44 wt. % Pd and 2.3 wt. % N.

EXAMPLE 3

Pd/Na/A36 (Catalyst C)

The procedure of Example 1 is repeated except that 10.45 g of sodium dihydrogen phosphate is used with 28.9 g Pd/A36 catalyst. The product (Catalyst C) contains 0.35 wt. % Pd and 6.0 wt. % Na.

EXAMPLE 4

Pd/K/A36 (Catalyst D)

The procedure of Example 1 is repeated except that 4.46 g of potassium dihydrogen phosphate is used with 29.4 g Pd/A36 catalyst. The product (Catalyst D) contains 0.29 wt. % Pd and 3.9 wt. % K.

EXAMPLE 5

Pd/K/A36 (Catalyst E)

The procedure of Example 1 is repeated except that 8.9 g of potassium dihydrogen phosphate is used with 29.3 g Pd/A36 catalyst. The product (Catalyst E) contains 0.31 wt. % Pd and 8.0 wt. % K.

EXAMPLE 6

Pd/Mg/A36 (Catalyst F)

The procedure of Example 1 is repeated except that 8.47 g of $Mg(NO_3)_2 \cdot 6H_2O$ is used with 20.0 g of Pd/A36 catalyst. The product (Catalyst F) contains 0.40 wt. % Pd and 3.1 wt. % Mg.

EXAMPLE 7

Pd/A36 (Catalyst G)

The procedure of Example 1 is repeated except that the cation-exchange step is omitted. The product (Catalyst G) contains 0.45 wt. % Pd.

EXAMPLE 8

Pd/A36 (Catalyst H)

The procedure of Example 1 is repeated except that the cation exchange step is omitted. The product (Catalyst H) contains 0.40 wt. % Pd.

EXAMPLES 9-17

Epoxidation of Propylene in the Presence of Buffer

An ammonium phosphate buffer solution (0.1 M, pH 6) is prepared as follows. Ammonium dihydrogen phosphate (11.5 g) is dissolved in 900 g of deionized water. Aqueous ammonium hydroxide (30 wt. % $NH_4OH$) is added to the solution until the pH reads 6 via a pH meter. The volume of the solution is then increased to exactly 1000 mL with additional deionized water.

Titanium silicalite-1 (TS-1) samples are prepared by following procedures disclosed in U.S. Pat. Nos. 4,410,501 and 4,833,260.

A 300-mL stainless steel reactor is charged with 0.20 g of catalyst (see Table 1 for catalyst used), 0.50 g of TS-1 powder (Ti wt. % of TS-1 samples are listed in Table 1), 13 g of buffer solution as prepared above, and 100 g of methanol. The reactor is then charged to 300 psig with a feed gas consisting of 2 volume percent (vol. %) hydrogen, 4 vol. % oxygen, 5 vol. % propylene, 0.5 vol. % methane, and the balance nitrogen. The pressure in the reactor is maintained at 300 psig via a back pressure regulator with the feed gases passed continuously through the reactor at 1600 mL/min (measured at 23° C. and 1 atmosphere pressure). In order to maintain a constant solvent level in the reactor during the run, the oxygen, nitrogen and propylene feeds are passed through a 2-L stainless steel vessel (saturator) preceding the reactor containing 1.5 L of methanol. The reaction mixture is heated to 60° C. while it is stirred at 1500 rpm. The gaseous effluent is analyzed by an online gas chromatograph (GC) every hour and the liquid analyzed by offline GC at the end of the 18 h run. The products formed include propylene oxide (PO), propane, and derivatives of propylene oxide such as propylene glycol, propylene glycol monomethyl ethers, dipropylene glycol, and dipropylene glycol methyl ethers. The results are shown in Table 1. The catalyst productivity is defined as the grams of PO formed (including PO which is subsequently reacted to form PO derivatives) per gram of catalysts (TS-1 and Pd/A36 catalyst) per hour. POE (mole)=moles of PO+moles of PO units in the PO derivatives. PO/POE=(moles of PO)/(moles of POE)× 100. Propylene to POE selectivity=(moles of POE)/(moles of propane formed+moles of POE)×100.

Results show that reacting propylene, hydrogen, and oxygen in the presence of TS-1 and a Pd/A36 catalyst is effective in producing propylene oxide. A catalyst comprising a cation-exchanged resin further improves the productivity and/or the selectivity of the process.

EXAMPLE 18

Epoxidation of Propylene in the Absence of Buffer

The procedure of Examples 9-17 is repeated except that 13 g of deionized water is used instead of buffer solution. Results appear in Table 1.

Comparison between Examples 17 and 18 shows the advantage of using a buffer in the present epoxidation process.

TABLE 1

| | Epoxidation of Propylene | | | | | | | | | |
|---|---|---|---|---|---|---|---|---|---|---|
| | Example | | | | | | | | | |
| | 9 | 10 | 11 | 12 | 13 | 14 | 15 | 16 | 17 | 18** |
| Pd Catalyst | G | B | H | A | B | C | D | E | F | F |
| Pd, wt. % | 0.45 | 0.44 | 0.40 | 0.44 | 0.44 | 0.35 | 0.29 | 0.31 | 0.40 | 0.40 |
| Exchanged Cation | none | $NH_4^+$ | none | $Na^+$ | $NH_4^+$ | $Na^+$ | $K^+$ | $K^+$ | $Mg^{2+}$ | $Mg^{2+}$ |
| Cation, wt. % | | 2.3* | | 4.0 | 2.3* | 6.0 | 3.9 | 8.0 | 3.1 | 3.1 |
| Pd Catalyst Amount, g | 0.20 | 0.20 | 0.15 | 0.15 | 0.15 | 0.15 | 0.15 | 0.15 | 0.15 | 0.15 |
| TS-1, Ti wt. % | 2.0 | 2.0 | 1.8 | 1.8 | 1.8 | 1.8 | 1.8 | 1.8 | 1.8 | 1.8 |
| Catalyst Productivity, g POE/g cat/h | 0.46 | 0.49 | 0.29 | 0.36 | 0.36 | 0.28 | 0.38 | 0.29 | 0.27 | 0.20 |
| PO/POE, % (mole/mole) | 75 | 84 | 86 | 90 | 90 | 91 | 90 | 91 | 90 | 37 |
| Propylene to POE Selectivity, % (mole/mole) | 68 | 77 | 68 | 77 | 77 | 70 | 70 | 81 | 77 | 16 |

*wt. % of N.
**No buffer is used

We claim:

1. An epoxidation process comprising reacting an olefin, hydrogen, and oxygen in the presence of an oxidation catalyst comprising a transition metal zeolite, and a noble metal catalyst comprising a noble metal and an ion-exchange resin.

2. The process of claim 1 wherein the transition metal zeolite is a titanium zeolite.

3. The process of claim 1 wherein the transition metal zeolite is TS-1.

4. The process of claim 1 wherein the noble metal is selected from the group consisting of palladium, platinum, gold, rhenium, silver, and mixtures thereof.

5. The process of claim 1 wherein the ion-exchange resin has a capacity of from 0.1 to 20 eq/kg.

6. The process of claim 1 wherein the ion-exchange resin has a capacity of from 1 to 10 eq/kg.

7. The process of claim 1 wherein the ion-exchange resin is an acidic ion-exchange resin.

8. The process of claim 7 wherein the ion-exchange resin is a sulfonic acid polystyrene resin.

9. The process of claim 7 wherein the ion-exchange resin comprises a cation selected from the group consisting of alkali metal, alkaline earth metal, lanthanide metal, zinc, cadmium, ammonium, alkylammonium, and alkylphosphonium ions, and mixtures thereof.

10. The process of claim 7 wherein the ion-exchange resin comprises a cation selected from the group consisting of alkali metal and alkaline earth metal ions, and mixtures thereof.

11. The process of claim 7 wherein the ion-exchange resin comprises a cation selected from the group consisting of sodium, potassium, calcium, and magnesium ions, and mixtures thereof.

12. The process of claim 1 wherein the noble metal catalyst further comprises a support component selected from the group consisting of carbon, titania, zirconia, niobia, silica, alumina, silica-alumina, titania-silica, zirconia-silica, niobia-silica, and mixtures thereof.

13. The process of claim 1 wherein the reaction is performed in the presence of a solvent.

14. The process of claim 13 wherein the solvent is selected from the group consisting of alcohols, ethers, esters, ketones, carbon dioxide, water, and mixtures thereof.

15. The process of claim 13 wherein the reaction is performed in the presence of a buffer.

16. The process of claim 15 wherein the buffer comprises an anion selected from the group consisting of phosphate, carbonate, sulfate, hydroxide, acetate, and mixtures thereof; and a cation selected from the group consisting of ammonium, alkylammonium, alkylphosphonium, alkali metal, and alkaline earth metal ions, and mixtures thereof.

17. The process of claim 1 wherein the olefin is one or more $C_2$-$C_6$ olefins.

18. The process of claim 1 wherein the olefin is propylene.

19. An epoxidation process comprising reacting propylene, hydrogen, and oxygen in a solvent in the presence of a buffer, an oxidation catalyst comprising a titanium zeolite, and a noble metal catalyst comprising a noble metal and a sulfonic acid polystyrene resin.

20. The process of claim 19 wherein the sulfonic acid polystyrene resin comprises a cation selected from the group consisting of alkali metal and alkaline earth metal ions, and mixtures thereof.

* * * * *